United States Patent [19]
Schleitweiler et al.

[11] Patent Number: 5,437,193
[45] Date of Patent: Aug. 1, 1995

[54] METHOD AND APPARATUS FOR TESTING MICROFILAMENTS

[75] Inventors: Patrick M. Schleitweiler, Dayton; Charles W. Merten, Jr., West Carrollton, both of Ohio

[73] Assignee: The United States of America as represented by the United States Department of Energy, Washington, D.C.

[21] Appl. No.: 216,521

[22] Filed: Mar. 22, 1994

[51] Int. Cl.$^6$ ............................................. G01N 3/00
[52] U.S. Cl. .................................. 73/830; 73/856
[58] Field of Search ...................... 73/826, 827–831, 73/856

[56] References Cited

U.S. PATENT DOCUMENTS

| | | | |
|---|---|---|---|
| 2,377,869 | 6/1945 | Elliott | 73/826 |
| 3,324,713 | 6/1967 | Krock et al. | 73/828 |
| 3,379,054 | 4/1968 | Folweiler | 73/828 |
| 3,572,108 | 3/1971 | McShane et al. | 73/827 |
| 3,602,040 | 8/1971 | Shulze | |
| 3,667,288 | 6/1972 | Hargreaves | |
| 3,969,930 | 7/1976 | Prevorsek et al. | 73/826 |
| 4,909,084 | 3/1990 | Knoff | |

Primary Examiner—Robert Raevis
Attorney, Agent, or Firm—Russell D. Elliott; James H. Chafin; William R. Moser

[57] ABSTRACT

A method and apparatus are disclosed for testing tensile strength of microfilaments. Fibers as small as 0.001 inch in diameter and 0.04 inches in length have been tested, although the method and apparatus of the invention are capable of testing fibers of smaller diameter and length. The invention utilizes a method wherein one or both ends of a microfilament is gripped using resin which is softened sufficiently to accept an end of the microfilament and then allowed to harden. The invention also employs the use of a translation stage capable of controlled three-dimensional movement suited to facilitating gripping of the microfilament.

12 Claims, 2 Drawing Sheets

METHOD AND APPARATUS FOR TESTING MICROFILAMENTS

GOVERNMENT RIGHTS

The United States Government has rights in this invention pursuant to Contract No. DE-AC04-88DP43495 between the U.S. Department of Energy (DOE) and EG&G Mound Applied Technologies.

BACKGROUND OF THE INVENTION

1. FIELD OF INVENTION

This invention relates generally to the field of tensile testing of filaments and, more particularly, to a method and apparatus for testing microfilaments. Fibers as small as 0.001 inches in diameter and 0.040 inches in length have been tested, although the method and apparatus of the invention are capable of testing fibers of smaller diameter and length.

2. DESCRIPTION OF THE RELATED ART

Fibrous materials are used in a variety of applications both to provide reinforcement in composite matrices and as conduits in electronic components. In recent years, many new fibrous materials have been developed which are manufactured from both natural and synthetic components. Types of fibers used, for example, to reinforce plastic include glass, ceramic and polymeric fibers such as aramids. Useful fibers are available in a wide range of lengths and diameters suited to various applications and manufacturing techniques. In addition to size, the durability of fibers and their ability to withstand mechanical forces such as bending or pulling are determining factors with regard to their potential uses.

Tensile strength is one characteristic which is commonly tested in assessing suitability of fibers for particular applications. There are a number of instances in the prior art of methods and apparatuses for testing the tensile strength of fibers. Special fixtures are commercially available to test wire, rope and cable which generally include a gripping arrangement involving wrapping the specimen around a mandrel or capstan to avoid crimping or kinking the material which could affect the results of tests. This assumes that the sample is long and flexible enough to be successfully wrapped around a mandrel.

The ability to test small fibers is becoming increasingly important as scientists and engineers begin to model the complex mechanical properties of fiber-reinforced, composite materials. Tensile testing of microfilament specimens is, however, difficult and tedious since small. diameter, delicate specimens require special handling techniques. Although considerable effort has been expended in the past to develop test methods and equipment to facilitate the testing of fine, small diameter specimens (see, for example, W. F. Knoff, U.S. Pat. No. 4,909,084; J. E. Hargraves, U.S. Pat. No. 3,667,288, and C. E. Shulze, U.S. Pat. No. 3,602,040), problems of alignment, gripping and control still present significant challenges, especially for fibers of short length. To date, a satisfactory microfilament tensile testing system has not been developed which is capable of testing short, small diameter samples (on the order of 0.04 in. length × 0.001 in. diameter).

BRIEF SUMMARY OF THE INVENTION

Disclosed here are embodiments of an apparatus and method capable of overcoming problems associated with gripping and testing microfilaments. According to the invention, a microfilament can be gripped by inserting it into a droplet of softened resin which then is allowed to harden. The invention further provides the capability to perform this insertion precisely with respect to positioning and then, after the microfilament is appropriately gripped, to test it by subjecting it to tensile stress which is monitored using a load cell.

Accordingly, it is an object of the present invention to provide a method and apparatus for testing tensile strength of a microfilament specimen.

It is another object of the present invention to provide such a testing apparatus having the capability to conveniently manipulate the position of the load cell and load train according to X-, Y- and Z- axes using a translation stage.

It is yet another object of the present invention to provide a method for gripping at least one end of a microfilament specimen using resin which is softened sufficiently to accept the end of the specimen and subsequently allowed to harden.

Upon further study of the specification and appended claims, further objects and advantages will become apparent to those skilled in the art.

DETAILED DESCRIPTION OF THE INVENTION

Figure 1:
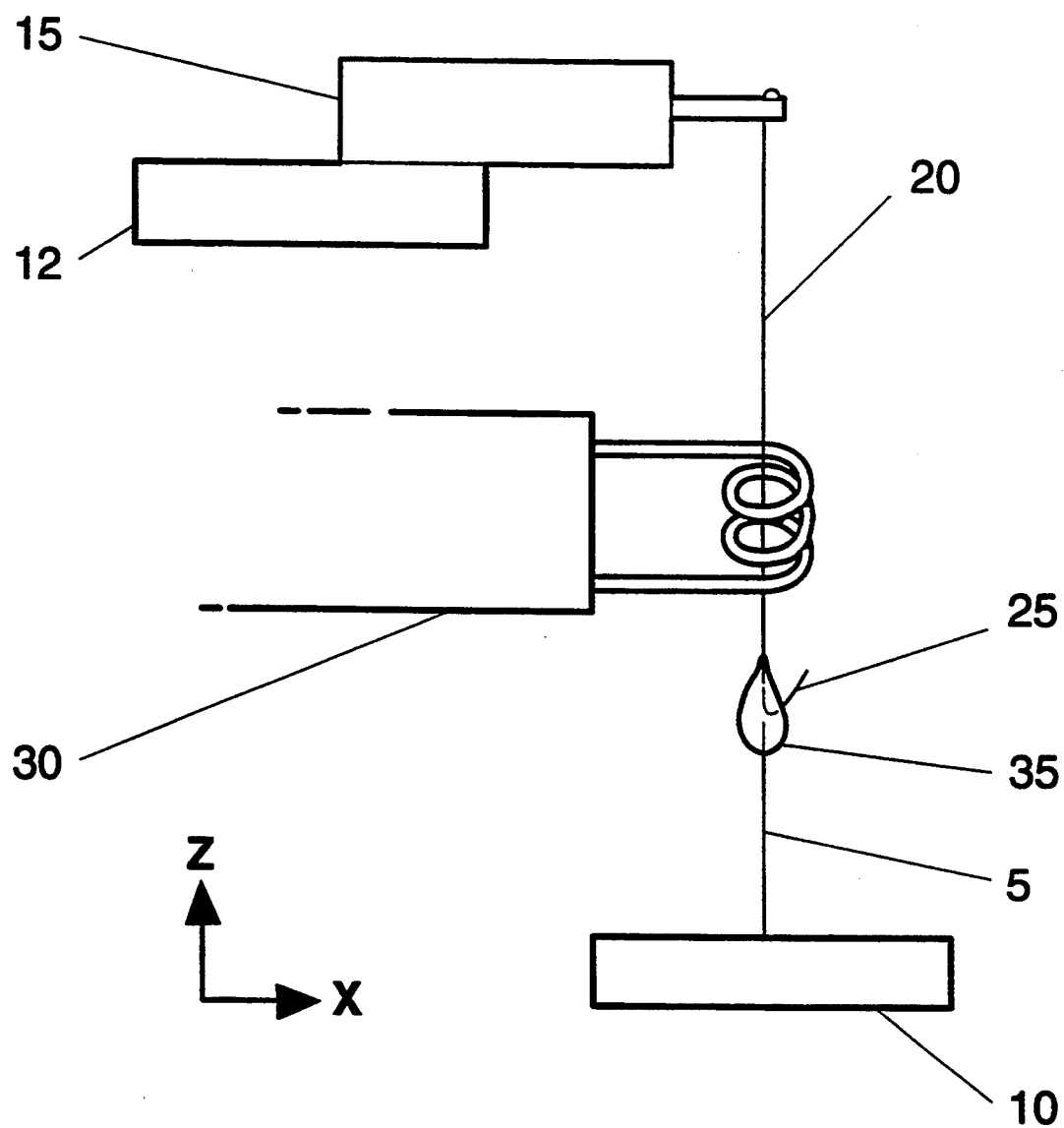
FIG. 1 is a schematic illustration of a preferred embodiment of the load train of the invention.

According to the method of the invention a microfilament can be gripped at either one end or both ends using a droplet of softened resin into which the fiber is inserted. After the resin hardens, a satisfactory grip is achieved which can hold a specimen adequately to permit testing of the fiber's tensile strength characteristics. Advantages associated with this method of gripping include minimizing stress placed on the fiber as a result of gripping, and in the context of the best mode described here, the capability to achieve gripping of the microfilament without interfering with the load train of a tensile testing apparatus. This is illustrated in FIG. 1. In a preferred embodiment, insertion is achieved by means of a translation stage supporting the load train which, at a minimum, is capable of movement along the axis of the fiber, permitting movement of the resin droplet from a position wherein the fiber is outside the resin droplet to a position wherein the end of the fiber penetrates the resin droplet. In the best mode, the translation stage, in addition to moving in a direction parallel to the axis of the fiber, is capable of movement within a plane perpendicular to the fiber permitting greater freedom in aligning the droplet with respect to the fiber.

Figure 2:
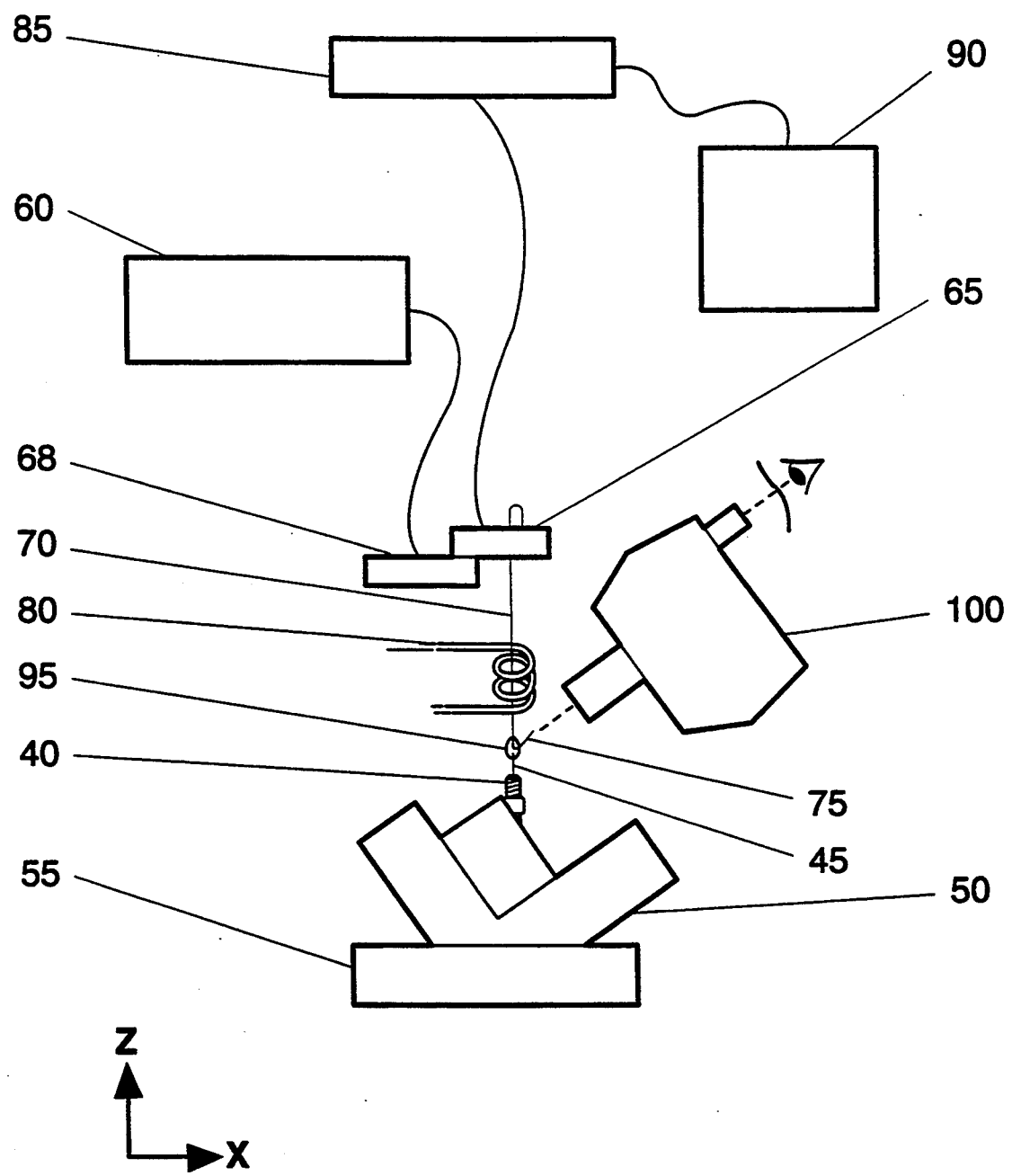
FIG. 2 is a schematic illustration showing a preferred embodiment of an experimental set-up used in the method of the invention.

As mentioned, due to the small. size and delicate nature of the fibers to be tested using the method and apparatus of this invention, it may be appropriate to use the resin gripping technique at both ends of the fiber. In other instances, however, small diameter fibers may be of sufficient length to allow affixing one end to components by welding, for example, and then gripping the remaining end with the resin gripping technique of this invention. Such a case is illustrated in FIG. 2. In addition, the resin gripping technique may be adapted for gripping and pulling microfilaments in evaluating postmortem weld integrity or testing microfilament attachment within a matrix such as in the case of fiber glass.

FIG. 1 illustrates a preferred embodiment for application of the resin gripping technique within the load train of a tensile testing apparatus. In the Figure, a microfilament 5 is affixed to a base 10. A precision load cell 15 is affixed to a translation stage 12 capable of movement according to an axis Z which is in alignment with the microfilament. The load cell supports a load wire 20 positioned in alignment with said axis Z. At the end of the load wire distal from the load cell is an irregularity 25 in the wire capable of supporting a droplet of resin. The irregularity in the example illustrated in FIG. 1 is in the form of a "shepherd's hook" although other forms of irregularity may suffice equally well. The load wire attached to the load cell and microfilament attached to the base define a load train aligned with the axis Z. Positioned about the load wire in proximity to the distal end bearing the irregularity is the coil of a resistance heater 30. According to the best mode, the coil is a nickel-chrome resistance heater, however, in other embodiments contemplated by this disclosure, other heating means may serve to adequately soften resin.

According to the preferred embodiment of the method, the coil of the resistance heater 30 is heated to allow the irregularity 25 in the loading wire 20 to attain a temperature sufficient to soften low-melting point resin. A sufficient quantum of such low-melting point resin is then allowed to touch the irregularity such that a droplet 35 of the resin forms and adheres to the wire 20. According to the best mode, glycol phthalate (GP) polyester resin is used as the gripping media. GP is commercially available as Stronghold TM 7036 (J. H. Young Company, Inc., Rochester, N.Y.). This type of polyester resin has a low softening temperature and hardens within a few seconds after a heat source is removed. In other embodiments contemplated by this disclosure, other gripping media may adequately serve the gripping function.

After a droplet of softened resin is formed in the region of the distal end of the load wire 20, the free end of the microfilament 5 is inserted into the droplet 35. The resistance heater 30 is then turned off and the microfilament is held in the inserted position long enough to allow the resin droplet to cool and harden sufficiently to grip the inserted microfilament. Finally, the tensile strength of the microfilament 5 may be tested by pulling the load cell 15 in a direction along the axis Z away from the base 10 sufficiently to generate desired data. The tensile strain associated with the testing may or may not be sufficient to break the microfilament, depending on the test requirements.

Referring to FIG. 2, a component 40 with a microfilament 45 attached at one end is supported in a vise and V-block assembly 50 which in turn is supported by a magnetic base 55. For the purpose of clarity in this schematic illustration, the microfilament is shown much larger than it would otherwise be according to the scale of the Figure. The vise and V-block assembly is used for convenience of gross manipulation of the component 40. Although the vise and V-block assembly provides great flexibility for specimen positioning for microfilament specimen testing, this disclosure also contemplates the use of other appropriate means for adjoining the microfilament to the translation stage, depending on the particular application.

The magnetic base 55 in this instance is capable of two-dimensional movement according to the axis X depicted in the Figure and a second axis Y passing through the plane of the Figure. The axis X and the axis Y together define a plane which is perpendicular to the axis Z. In the best mode contemplated by this disclosure, the load cell 65 and associated translation stage 68 are capable of three-dimensional movement according to the axes X, Y and Z. The x-axis positioning of the load cell 65 is motor driven and controlled remotely by a stage controller 60 in operative association with the translation stage 68.

Also depicted in the Figure is the precision load cell 65 in operative association with a digital load readout 85 and a plotting system 90. Attached to the load cell is a load wire 70 which is in alignment with the axis Z. Similar to the arrangement depicted in FIG. 1, the load wire bears a shape irregularity 75 at the end distal to the load cell, and a resistance heater 80 in the shape of a coil is positioned about the load wire in proximity to the irregularity. The coil of the resistance heater is positioned such that it does not touch the load wire or otherwise interfere with the load train defined by the load cell, the load wire and the microfilament.

According to the method of the invention, the resistance heater 80 is activated and the load wire 70 is heated sufficiently to soften resin applied to the shape irregularity 75. The resin thus forms a droplet 95 into which the free end of the microfilament 45 is inserted. Insertion of the microfilament is achieved by manipulating the position of the load cell 65 and consequently the position of the load wire 70 and droplet 95. Finally, the Figure illustrates the use of a stereo microscope 100 to provide magnification and to assist the operator in the insertion effort. After appropriate insertion of the microfilament into the resin droplet is achieved, the resistance heater is turned off, the resin is allowed to cool, and the microfilament specimen may then be tested for tensile strength by moving the load cell 65 along the axis Z in a direction away from the magnetic base 55.

The foregoing description of the invention has been presented for purposes of illustration. It is not intended to be exhaustive or to limit the invention to the precise forms disclosed. Obvious modifications or variations are possible in light of the above teachings. The embodiments were chosen and described in order to best illustrate the principles of the invention and its practical application to thereby enable one of ordinary skill in the art to best utilize the invention in various embodiments and with various modifications as are suited to the particular use contemplated, as long as the principles described herein are followed. Thus, changes can be made in the above-described invention without departing from the spirit and scope thereof. It is also intended that the scope of the invention be defined by the claims appended hereto. The invention is intended to encompass all such variations as fall within its spirit and scope.

We claim:

1. An apparatus for testing tensile strength of a microfilament specimen having a first and second end comprising:

a load cell with an associated translation stage, a first attaching means for attaching said first end of said microfilament specimen to said load cell, said first attaching means comprising a loading wire including first and second ends, said first end of said loading wire being attached to said load cell, and resin positioned on said second end of said loading wire, said resin providing means for receiver said first end of said microfilament specimen to said loading wire, a second attaching means for attaching said second end of said microfilament specimen to a base, and a means for moving said load cell via said translation stage in a linear direction, defining a Z-axis, either toward or away from said base.

2. The apparatus of claim 1 further comprising a heating means associated with said loading wire.

3. The apparatus of claim 2 wherein said heating means comprises an electrical resistance heater capable of softening said resin.

4. The apparatus of claim 3 wherein said electrical resistance heater comprises a wire coil defining a center axis, said wire coil being positioned about said shaft of said loading wire in proximity to said second end of said loading wire with said center axis of said coil substantially aligned with said shaft of said loading wire.

5. The apparatus of claim 4 wherein said load cell is capable of movement within a plane defined by perpendicular X- and Y-axes, which plane is perpendicular to said Z-axis.

6. The apparatus of claim 5 further comprising a magnification means.

7. The apparatus of claim 6 wherein said magnification means is a microscope.

8. A method for testing tensile strength of a microfilament specimen having a first and second end comprising the steps of:

attaching said second end of said microfilament specimen to a base, attaching said first end of said microfilament specimen to a load cell by affixing one end of a loading wire comprising two ends to said load cell, positioning on the opposite end of said loading wire a sufficient amount of resin to form a droplet when heated to softening, heating said resin sufficiently to cause it to soften, inserting said first end of said microfilament specimen into said resin, and allowing said resin to cool and-harden, and pulling said load cell, with said microfilament specimen attached, in a linear direction in alignment with said microfilament specimen away from said base thereby exerting tensile strain on said microfilament specimen.

9. The method of claim 8 wherein said tensile strain is sufficient to break said microfilament specimen.

10. The method of claim 8 wherein said tensile strain is not sufficient to break said microfilament specimen.

11. The method of claim 8 wherein said insertion step is facilitated by magnification using optical magnification.

12. The method of claim 11 wherein said optical magnification is provided by a microscope.

* * * * *